(12) United States Patent
Kokeguchi

(10) Patent No.: US 8,094,360 B2
(45) Date of Patent: Jan. 10, 2012

(54) ROOM TEMPERATURE MOLTEN SALT AND DISPLAY ELEMENT

(75) Inventor: Noriyuki Kokeguchi, Tokyo (JP)

(73) Assignee: Konica Minolta Holdings, Inc. (JP)

( * ) Notice: Subject to any disclaimer, the term of this patent is extended or adjusted under 35 U.S.C. 154(b) by 1012 days.

(21) Appl. No.: 11/995,882

(22) PCT Filed: Apr. 6, 2006

(86) PCT No.: PCT/JP2006/307305
§ 371 (c)(1),
(2), (4) Date: Jan. 16, 2008

(87) PCT Pub. No.: WO2007/010653
PCT Pub. Date: Jan. 25, 2007

(65) Prior Publication Data
US 2009/0091234 A1    Apr. 9, 2009

(30) Foreign Application Priority Data

Jul. 19, 2005    (JP) ................. 2005-208375

(51) Int. Cl.
*G02F 1/15*    (2006.01)
*G09G 3/19*    (2006.01)
*H04N 9/16*    (2006.01)
(52) U.S. Cl. ............... 359/265; 359/49; 348/817
(58) Field of Classification Search .......... 359/240, 359/247, 250, 253, 265–267, 315, 318, 321; 345/49, 105; 348/817
See application file for complete search history.

(56) References Cited

U.S. PATENT DOCUMENTS

| | | |
|---|---|---|
| 4,240,716 A | 12/1980 | Camlibel et al. |
| 4,357,396 A | 11/1982 | Grunewalder et al. |
| 2005/0206994 A1* | 9/2005 | Kokeguchi et al. ........... 359/296 |

FOREIGN PATENT DOCUMENTS

| | | |
|---|---|---|
| DE | 10124002 C1 | 2/2003 |
| EP | 1887419 A1 | 2/2008 |
| JP | 60-187695 A | 9/1985 |
| JP | 11-269691 A | 10/1999 |
| JP | 2000-192279 A | 7/2000 |
| JP | 2003-15164 A | 1/2003 |
| JP | 3428603 | 5/2003 |
| JP | 2003-241227 | 8/2003 |

OTHER PUBLICATIONS

European Search Report for Japanese Application No. 06731253.8—1211/1914225 dated Jul. 9, 2010.

* cited by examiner

*Primary Examiner* — Dwayne Pinkney
(74) *Attorney, Agent, or Firm* — Cantor Colburn LLP

(57) ABSTRACT

A salt molten at room temperature that does not contain any organic solvent, excelling in stability; and a display device that is improved in the durability in high-temperature environment by virtue of the use thereof. There is provided a salt molten at room temperature characterized by being composed of a silver salt and any of compounds of the following general formula (I) or general formula (II).

16 Claims, 1 Drawing Sheet

US 8,094,360 B2

ROOM TEMPERATURE MOLTEN SALT AND DISPLAY ELEMENT

CROSS REFERENCE TO RELATED APPLICATIONS

Figure 1:
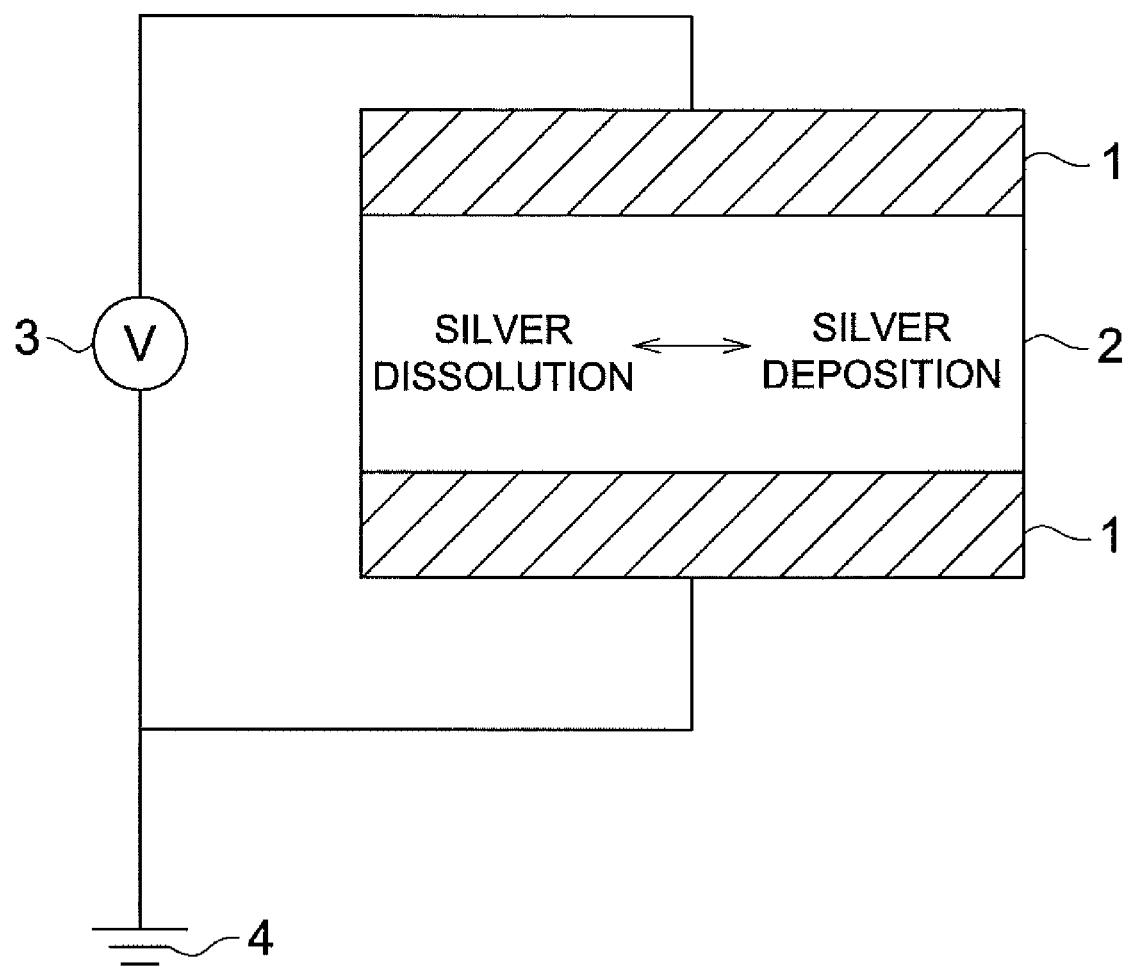

This is a U.S. national stage of application No. PCT/JP2006/307305, filed on 6 Apr., 2006. Priority under 35 U.S.C. §119(a) and 35 U.S.C. §365(b) is claimed from Japanese Application No. 2005-208375, filed 19 Jul., 2005, the disclosure of which is also incorporated herein by reference.

TECHNICAL FIELD

The present invention relates to A room temperature molten salt and an electrochromic display element utilizing silver dissolution and deposition employing it.

BACKGROUND

In recent years, along with enhancement of the operation rate of personal computers, and popularization of network infrastructure, as well as an increase in capacity of data storage and a decrease in its cost, occasions have increasingly occurred in which pieces of information such as documents and images, which have been provided in the form of paper printed matter, are received as simpler electronic information and viewed as received electronic information.

As viewing means for such electronic information, mainly employed are those of light emitting types such as conventional liquid crystal displays and CRTs or recent organic EL displays. Specifically, when electronic information includes document information, it is required to watch any of the above viewing means for a relatively long period. However, it is hardly stated that the above viewing means are human friendly. It is common knowledge that light emitting type displays result in problems such as eye fatigue due to flicker, inconvenient portability, limitations in reading posture, necessity to look at still images, or an increase in power consumption.

As means to overcome the above drawbacks, are known reflection type displays (having memory function) which utilize outside light and consume no power to maintain images. However, it is difficult to state that due to the following reasons, they exhibit sufficient performance.

Namely, a system employing polarizing plates, such as a reflection type liquid crystal, results in a problem for a white display due to a low reflectance of approximately 40%. In addition, it is difficulty to state that most methods to produce structuring members are simple and easy. Further, polymer dispersion type liquid crystals require high voltage and the contrast of the resulting images is insufficient due to utilizing the difference in refractive indices between organic compounds. Still further, polymer network type liquid crystals result in problems such as application of high voltage and requirement of complicated TFT circuitry to enhance memory capability. Yet further, display elements employing electrophoresis require high voltage of at least 10 V and tend to suffer insufficient durability due to aggregation of electrophoretic particles. Further, electrochromic display elements, though being drivable at a low voltage of at most 3 V, result in insufficient color quality of black and common colors (namely yellow, magenta, cyan, blue, and red) and tend to result in problems such that, in order to secure memory capability, the display cell requires a complicated film structure such as vapor deposition film.

As a display system, which overcomes the drawbacks of each of the above systems, an electrodeposition (hereinafter referred to as ED) system has been known which utilizes dissolution and deposition of metals or salts thereof. ED systems exhibit advantages such as drivability at a low voltage of at most 3 V, a simple cell structure, excellent black and white contrast, or excellent black quality, for which various methods have been disclosed (refer, for example, to Patent Documents 1-3).

The inventors of the present invention conducted detailed investigation of technologies disclosed in each of the above Patent Documents, and came upon the following problems. In conventional technologies, the electrolyte contains an organic solvent, sealing capability of the display element during storage over an extended period at a high temperature ambience destroyed whereby liquid leaks out, and causes contamination of circumference, or the organic solvent permeates or volatiles into sealing agent to cause change of electrolyte composition and display characteristics varies.

Patent Document 1: U.S. Pat. No. 4,240,716
Patent Document 2: Japanese Patent No. 3428603
Patent Document 3: Japanese Patent Publication Open to Public Inspection (hereinafter referred to as JP-A) 2003-241227

SUMMARY OF THE INVENTION

Problems to be Dissolved

In view of the foregoing, the present invention was achieved. An object of the present invention is to provide a room temperature molten salt, which does not contain any organic solvent, excelling in stability, and a display element which is improved in durability in high temperature environments by virtue of the use thereof.

Technical Means to Dissolve the Problem

The above object of the present invention was archived via the following embodiments.

1. A room temperature molten salt which is characterized by being formed from a silver salt and a compound represented by the following Formulas (I) or (II).

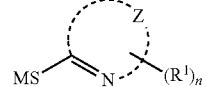

Formula (I)

wherein M represents a hydrogen atom, a metal atom, or a quaternary ammonium; Z represents a nitrogen containing heterocyclic ring excluding imidazole rings; n represents 0-5; $R^1$ represents a hydrogen atom, a halogen atom, an alkyl group, an aryl group, an alkylcarbonamido group, an arylcarbonamido group, an alkylsulfonamido group, an arylsulfonamido group, an alkoxy group, an aryloxy group, an alkylthio group, an arylthio group, an alkylcarbamoyl group, an arylcarbamoyl group, a carbamoyl group, an alkylsulfamoyl group, an arylsulfamoyl group, a sulfamoyl group, a cyano group, an alkylsulfonyl group, an arylsulfonyl group, an alkoxycarbonyl group, an aryloxycarbonyl group, an alkylcarbonyl group, an arylcarbonyl group, an acyloxy group, a carboxyl group, a carbonyl group, a sulfonyl group, an amino group, a hydroxyl group, or a heterocyclyl group; and when n is at least 2, any two or more of $R^1$ may be same or different and may be joined together to form a condensed ring.

$$R^2—S—R^3 \quad \text{Formula (II)}$$

wherein $R^2$ and $R^3$ each represent a substituted or unsubstituted hydrocarbon group, provided that when a ring containing an S atom is formed, an aromatic group is not included, and the atom adjacent to the S atom of $R^2$ and $R^3$ is not S.

2. The room temperature molten salt, described in 1., which is characterized in that a condition specified by the following Formula (3) is satisfied.

$$0.5 \leq S/M \leq 3.0 \quad \text{Formula (3)}$$

wherein M (in mol) represents a number of total mols of silver incorporated in the aforesaid room temperature molten salt and S (in mol) represents a number of total mols of the compound represented by Formula (I) or (II).

3. The room temperature molten salt, described in 1. or 2., which is characterized in that a condition specified by the following Formula (4) is satisfied.

$$0 \leq (X)/(Ag) \leq 0.01 \quad \text{Formula (4)}$$

wherein (X) (in mol/kg) represents mol concentration of a halogen ion or a halogen atom incorporated in the aforesaid room temperature molten salt, and (Ag) (in mol/kg) represents the total mol concentration of silver or silver in a compound containing silver in the chemical structure in the aforesaid room temperature molten salt.

4. The room temperature molten salt, described in any one of 1.-3., which is characterized in that the compound described by aforesaid Formula (I) is mercaptotriazole derivatives.

5. The room temperature molten salt, described in any one of 1.-4., which is characterized in that a molecular weight of the compound represented by aforesaid Formula (II) is 100-250.

6. In a display element which comprises, between the counter electrodes, an electrolyte containing silver or a compound containing silver in the chemical structure and the aforesaid counter electrodes are operated to result in dissolution and deposition of silver, the display element which is characterized in that the aforesaid electrolyte contains the room temperature molten salts described in any one of 1.-5.

7. The display element, described in 6., which is characterized in that the aforesaid electrolyte contains substantially no organic solvent.

8. The display element, described in 6. or 7., which is characterized in that the aforesaid driving operation initiates blackened silver deposition via application of voltage equal to or higher than the deposition overvoltage and continues deposition of blackened silver via application of voltage equal to or lower than the deposition overvoltage.

9. The display element, described in any one of 6.-8., which is characterized in that driving employed in the aforesaid driving operation is active matrix driving.

Advantage of the Invention

According to the present invention, it is possible to provide a room temperature molten salt, which does not contain any organic solvent, excelling in stability, and a display element which is improved in durability in high temperature environments by virtue of the use thereof.

BRIEF DESCRIPTION OF THE INVENTION

FIG. 1 is a schematic sectional view showing the basic structure of the display element of the present invention.

DESCRIPTION OF THE SYMBOLS 1 counter electrode
2 electrolyte
3 power source
4 grounding

OPTIMAL EMBODIMENT OF THE INVENTION

The optimal embodiment to practice the present invention will now be detailed.
(Room Temperature Molten Salts)

The room temperature molten salt of the present intention is characterized in being formed by employing silver salts and the compounds represented by above Formula (I) or silver salts and the compounds represented by above Formula (II).

The room temperature molten salt, as described in the present invention, is also called an ionic liquid and is a collective term which refers to the molten salt, which is a liquid containing cations and anions, exhibiting a melting point of at most 25° C., preferably at most 0° C., but more preferably at most −10° C.

Employed as silver salts to form the room temperature molten salts according to the present invention may be silver salts known in the art such as silver nitrate, silver carbonate, silver acetate, silver p-toluenesulfonate, silver perchlorate, silver trifluorosulfate, silver citrate, silver trifluoroacetate, silver iodide, silver chloride, silver bromide, silver sulfide, silver oxide, or fatty acid silver.

The compounds represented by above Formula (I), which form the room temperature molten salts of the present invention, will now be described.

In above Formula (I), M represents a hydrogen atom or quaternary ammonium; Z represents a nitrogen-containing heterocyclic ring except for imidazole rings; n represents an integer of 0-5; $R^1$ represents a hydrogen atom, a halogen atom, an alkyl group, an aryl group, an alkylcarbonamido group, an arylcarbonamido group, an alkylsulfonamido group, an arylsulfonamido group, an alkoxy group, an aryloxy group, an alkylthio group, an arylthio group, an alkylcarbamoyl group, an arylcarbamoyl group, a carbamoyl group, an alkylsulfamoyl group, an arylsulfamoyl group, a sulfamoyl group, a cyano group, an alkylsulfonyl group, an arylsulfonyl group, an alkoxycarbonyl group, an aryloxycarbonyl group, an alkylcarbonyl group, an arylcarbonyl group, an acyloxy group, a carboxyl group, a carbonyl group, a sulfonyl group, an amino group, a hydroxyl group, or a heterocyclyl group. When n represent at least 2, each $R^1$ may be the same or different, and may be joined to form a condensed ring.

Examples of metal atoms represented by M of Formula (I) include Li, Na, K, Mg, Ca, Zn, and Ag, while examples of quaternary ammonium include $NH_4$, $N(CH_3)_4$, $N(C_4H_9)_4$, $N(CH_3)_3C_{12}H_{25}$, $N(CH_3)_3C_{16}H_{33}$, and $N(CH_3)_3CH_2C_6H_5$.

Examples of the nitrogen-containing heterocyclic rings represented by Z of Formula (I) include a tetrazole ring, a triazole ring, an imidazole ring, an oxadiazole ring, a thiadiazole ring, an indole ring, an oxazole ring, a benzoxazole ring, a benzimidazole ring, a benzothiazole ring, a benzoselenazole ring, and a naphthoxazole ring.

Examples of the halogen atoms represented by $R^1$ of Formula (I) include a fluorine atom, a chlorine atom, a bromine atom and a iodine atom; examples of the alkyl groups include a methyl group, an ethyl group, a propyl group, an i-propyl group, a butyl group, a t-butyl group, a pentyl group, a cyclopentyl group, a hexyl group, a cyclohexyl group, an octyl group, a dodecyl group, a hydroxyethyl group, a methoxyethyl group, a trifluoromethyl group, and a benzyl group; examples of the aryl group include a phenyl group and a naphthyl group; examples of the alkylcarbonamido group include an acetylamino group, a propionylamino group, and a butyrylamino group; examples of the arylcarbonamido group include a benzoylamino group; examples of the alkylsulfonamido group include a methanesulfonylamino group and an ethanesulfonylamino group; examples of the arylsulfonamido group represented by the same include a benzenesulfonylamino group and a toluenesulfonylamino group; examples of the aryloxy group include a phenoxy group; examples of the alkylthio group include a methylthio group, an ethylthio group, and a butylthio group; examples of the arylthio group include a phenylthio group and a tolylthio group; examples of the alkylcarbamoyl group include a methylcarbamoyl group, a dimethylcarbamoyl group, an ethylcarbamoyl group, a diethylcarbamoyl group, a dibutylcarbamoyl group, a piperidylcarbamoyl group, and a morpholinylcarbamoyl group; examples of the arylcarbamoyl group include a phenylcarbamoyl group, a methylphenylcarbamoyl group, an ethylphenylcarbamoyl group, and a benzylphenylcarbamoyl group; examples of the alkylsulfamoyl group include a methylsulfamoyl group, a dimethylsulfamoyl group, an ethylsulfamoyl group, a dimethylsulfamoyl group, a dibutylsulfamoyl group, a piperidylsulfamoyl group, and a morphorylsulfamoyl group; examples of the arylsulfamoyl group include a phenylsulfamoyl group, a methylsulfamoyl group, an ethylphenylsulfamoyl group, and a benzylphenylsulfamoyl group; examples of the alkylsulfonyl group include a methanesulfonyl group and an ethanesulfonyl group; examples of the arylsulfonyl group include a phenylsulfonyl group, a 4-chlorophenylsulfonyl group, and a p-toluenesulfonyl group; examples of the alkoxycarbonyl group include a methoxycarbonyl group, an ethoxycarbonyl group, and a butoxycarbonyl group; examples of the aryloxycarbonyl group include a phenoxycarbonyl group; examples of the alkylcarbonyl group include an acetyl group, a propionyl group, and a butyroyl group; examples of the arylcarbonyl group include a benzoyl group and an alkylbenzoyl group; examples of the acyloxy group include an acetyloxy group, a propionyloxy group, and a butyroyloxy group; examples of the heterocyclyl group include an oxazole ring, a thiazole ring, a triazole ring, a selenazole ring, a tetrazole ring, an oxadiazole ring, a thiadiazole ring, a thiazine ring, a triazine ring, a benzoxazole ring, a benzothiazole ring, an indolenine ring, a benzoselenazole ring, a naphthothiazole ring, a triazaindolizine ring, a diazaindolizine ring, and a tetraazaindolizine ring. These substituents include those which have a substituent.

Specific examples of the preferred compounds represented by Formula (I) will now be cited, however the present invention is not limited thereto.

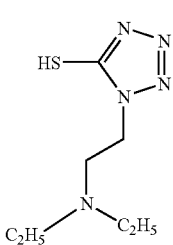

I-1

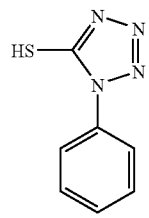

I-2

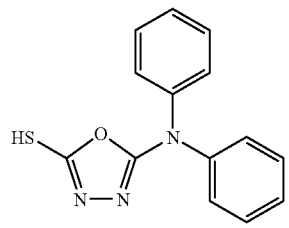

I-3

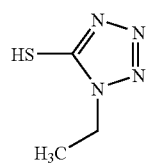

I-4

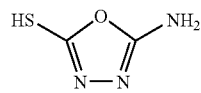

I-5

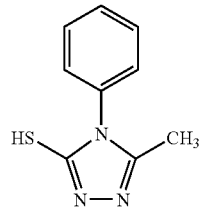

I-6

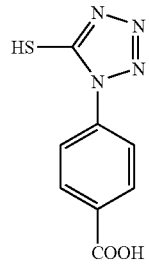

I-7

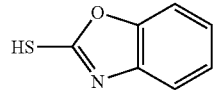

I-8

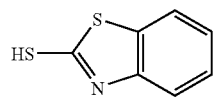

I-9

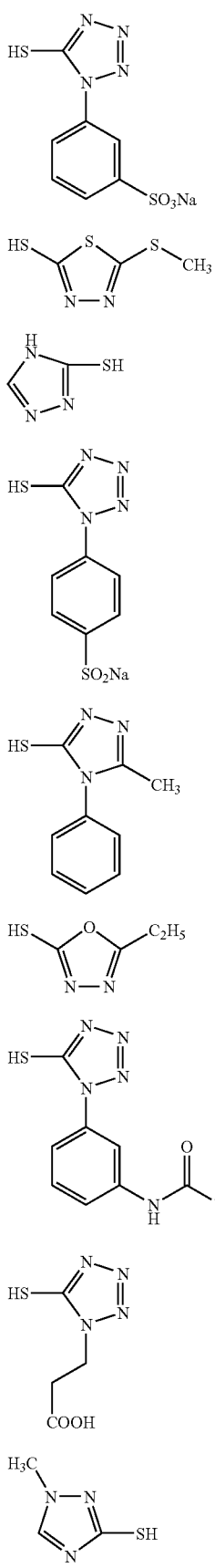

I-10
I-11
I-12
I-13
I-14
I-15
I-16
I-17
I-18

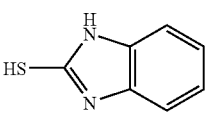

I-19

Preferred as compounds represented by Formula (I) according to the present invention are triazole derivatives having a mercapto group. In view of sufficiently realizing the targeted effects of the present invention, of these exemplified compounds, Exemplified Compounds I-12 and I-18 are particularly preferred.

The compounds exemplified by above Formula (II), which form the room temperature molten salt of the present invention, will now be described.

In above Formula (II), $R^2$ and $R^3$ each represent a substituted or unsubstituted hydrocarbon group, which includes an aromatic straight chain group or branched chain group. Further, these hydrocarbon groups may contain at least one of a nitrogen atom, an oxygen atom, a phosphorous atom, a sulfur atom, and a halogen atom. However, when a ring containing an S atom is formed, no aromatic group is employed. The atom adjacent to the S atom of $R^2$ and $R^3$ is not S.

Listed as a substitutable group to the hydrocarbon group may, for example, be an amino group, a guanidino group, a quaternary ammonium group, a hydroxyl group, a halogen compound, a carboxyl group, a carboxylate group, an amido group, a sulfinic acid group, a sulfonic acid group, a sulfate group, a phosphonic acid group, a phosphate group, a nitro group, and a cyano group.

It is commonly necessary to have silver solubilized in an electrolyte in order to result in dissolution and deposition of silver. For example, it is common to employ a method in which silver or silver-containing compound is modified to be soluble compound via coexistence of a compound containing chemical structure species which result in mutual interaction with silver, which forms a coordination bond with silver or forms a weak covalent bond with silver. Known as the above chemical structure species are a halogen atom, a mercapto group, a carboxyl group, an imino group and so on. In the present invention, a thioether group also usefully acts as a silver solvent and exhibits features such as minimal effects to coexisting compounds and high solubility in solvents.

Specific examples of the compounds represented by Formula (II) according to the present invention will now be cited, however the present invention is not limited to the exemplified compounds.

II-1: $CH_3SCH_2CH_2OH$
II-2: $HOCH_2CH_2SCH_2CH_2OH$
II-3: $HOCH_2CH_2SCH_2CH_2SCH_2CH_2OH$
II-4: $HOCH_2CH_2SCH_2CH_2SCH_2CH_2SCH_2CH_2OH$
II-5: $HOCH_2CH_2SCH_2CH_2OCH_2CH_2OCH_2CH_2SCH_2CH_2OH$
II-6: $HOCH_2CH_2OCH_2CH_2SCH_2CH_2SCH_2CH_2OCH_2CH_2OH$
II-7: $H_3CSCH_2CH_2COOH$
II-8: $HOOCCH_2SCH_2COOH$
II-9: $HOOCCH_2CH_2SCH_2CH_2COOH$
II-10: $HOOCCH_2SCH_2CH_2SCH_2COOH$
II-11: $HOOCCH_2SCH_2CH_2SCH_2CH_2SCH_2CH_2SCH_2COOH$
II-12: $HOOCCH_2SCH_2CH_2SCH_2CH(OH)CH_2SCH_2CH_2SCH_2CH_2COOH$
II-13: $HOOCCH_2SCH_2CH_2SCH_2CH(OH)CH(OH)CH_2SCH_2CH_2SCH_2CH_2COOH$

II-14: $H_3CSCH_2CH_2CH_2NH_2$
II-15: $H_2NCH_2CH_2SCH_2CH_2NH_2$
II-16: $H_2NCH_2CH_2SCH_2CH_2SCH_2CH_2NH_2$
II-17: $H_3CSCH_2CH_2CH(NH_2)COOH$
II-18: $H_2NCH_2CH_2OCH_2CH_2SCH_2CH_2SCH_2CH_2OCH_2CH_2NH_2$
II-19: $H_2NCH_2CH_2SCH_2CH_2OCH_2CCH_2OCH_2CH_2SCH_2CH_2NH_2$
II-20: $H_2NCH_2CH_2SCH_2CH_2SCH_2CH_2SCH_2CH_2SCH_2CH_2NH_2$
II-21: $HOOC(NH_2)CH_2CH_2CH_2SCH_2CH_2SCH_2CH_2CH(NH_2)COOH$
II-22: $HOOC(NH_2)CHCH_2SCH_2CH_2OCH_2CH_2OCH_2CH_2SCH_2CH(NH_2)COOH$
II-23: $HOOC(NH_2)CHCH_2OCH_2CH_2SCH_2CH_2SCH_2CH_2OCH_2CH(NH_2)COOH$
II-24: $H_2N(=O)CCH_2SCH_2CH_2OCH_2CH_2OCH_2CH_2SCH_2C(=O)NH_2$
II-25: $H_2N(O=)CCH_2SCH_2CH_2SCH_2C(O=)NH_2$
II-26: $H_2NHN(O=)CCH_2SCH_2CH_2SCH_2C(O=)NHNH_2$
II-27: $H_3(O=)NHCH_2CH_2SCH_2CH_2SCH_2CH_2NHC(O=)CH_2$
II-28: $H_2NO_2CH_2CH_2SCH_2CH_2SCH_2CH_2SO_2NH_2$
II-29: $NaO_3SCH_2CH_2CH_2SCH_2CH_2SCH_2CH_2SO_3Na$
II-30: $H_3CSO_2NHCH_2CH_2SCH_2CH_2SCH_2CH_2NHO_2SCH_3$
II-31: $H_2N(NH)CSCH_2CH_2SC(NH)NH_2 \cdot 2HBr$
II-32: $H_2(NH)CSCH_2CH_2OCH_2CH_2OCH_2CH_2SC(NH)NH_2 \cdot 2HCl$
II-33: $H_2N(NH)CNHCH_2CH_2SCH_2CH_2SCH_2CH_2NHC(NH)NH_2 \cdot 2HBr$
II-34: $[(CH_3)_3NCH_2CH_2SCH_2CH_2SCH_2CH_2N(CH_3)_3]^{2+} \cdot 2Cl^-$

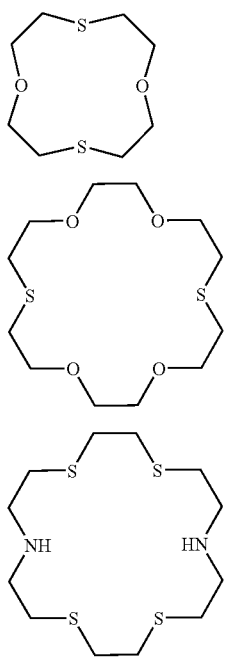

II-35

II-36

II-37

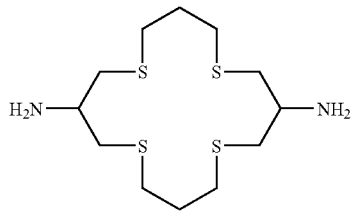

II-38

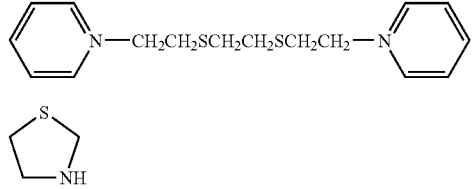

II-39

II-40

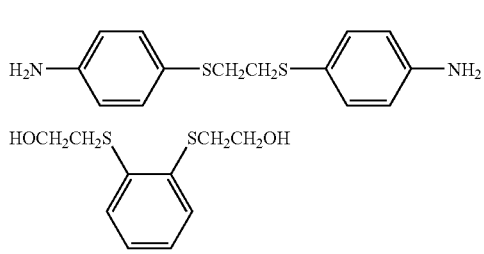

II-41

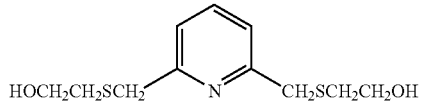

II-42

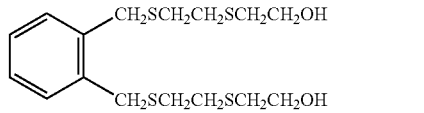

II-43

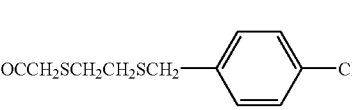

II-44

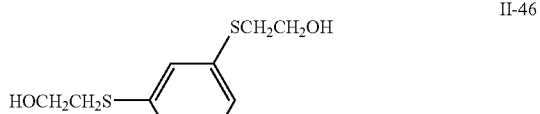

II-45

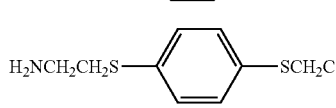

II-46

II-47

In view of compatibility with coexisting compounds and minimal generation of unpleasant odor, preferred as the compounds represented by Formula (II) according to the present invention are those having a molecular weight of 100-250. In view of sufficiently realizing the targeted effects of the present invention, of the above exemplified compounds Exemplified Compounds II-2 is particularly preferred.

Preparation methods of the room temperature molten salt containing silver salts of the present invention include, for example, 1) a method in which silver salts and the compounds represented by Formula (I) or (II) are mixed and the resulting mixture is heated to at least 120° C. to result in a molten state, followed by cooling, and 2) a method in which silver salts and the compounds represented by Formula (I) or (II) are mixed and dissolved in solvents followed by cooling after removal of the solvents via evaporation.

The room temperature molten salts of the present invention may be applied to display elements of electrochromic and electrodeposition, electrolytes of electrochemical elements such as dye sensitized solar batteries, lithium ion batteries, or electric double layer capacitor fuel batteries, solvents as the reaction field of particular synthetic reaction, electrolytic deposition reaction of minute metal particles, and raw materials to prepare a sintered body. In view of preparation of more homogeneous room temperature molten salts (prevention of non-uniformity due to formation of precipitates of insoluble materials during cooling after dissolution at high temperature), it is preferable that conditions specified by following Formula (3) are satisfied.

$$0.5 \leq S/M \leq 3.0 \qquad \text{Formula (3)}$$

wherein M (in mol) represents the number of total mols of silver contained in the room temperature molten salt of the present invention and S (in mol) represents the number of total mols of the compounds represented by Formula (I) or (II).

(Display Element)

The inventors of the present invention investigated means to minimize leakage of liquid due to the destruction of sealing capability of the display element during storage over an extended period at a high temperature ambience. As a result, discovered was the following and the present invention was achieved. By employing a display element having, between the counter electrodes, an electrolyte containing silver or compounds containing silver in the chemical structure, the counter electrodes were operated so that silver was dissolved and deposited. Further by employing a display element which was characterized in that the above electrolytes contains the above silver salts and the room temperature molten salts of the compound represented by above Formula (I), or the above silver salts and the room temperature molten slats of the compound represented by above Formula (II), a display element was realized which exhibited excellent durability at a high temperature ambience.

The display element of the present invention will now be detailed.

The display element of the present invention is an ED system display element which has, between the counter electrodes, an electrolyte containing silver or compounds containing silver in the chemical structure, while the counter electrodes are operated so that silver is dissolved and deposited.

In the display element of the present invention, it is preferable that the electrolyte containing the room temperature molten salt according to the present invention contains substantially no organic solvents. As used herein, "contains substantially no organic solvents" means that the content of organic solvents in the electrolyte is at most 5.0% by weight. The content is preferably at most 1.0% by weight, but it is specifically preferred that it contains no organic solvents.

In the display element of the present invention, by employing a novel room temperature molten salt composed of silver salts and mercapto compounds, or silver salts and thioether compounds, it is possible to make organic solvents conventionally incorporated in electrolytes almost unnecessary. As a result, it is characterized that it is possible to dramatically enhance durability of the display element by decreasing effects of destruction of sealing capability due to solvents.

(Compound Containing Silver, or Compound Containing Silver in Their Chemical Structure)

A compound containing silver, or a compound containing silver in their chemical structure, according to the present invention, is common designations of a compound such as silver oxide, silver sulfide, metallic silver, colloidal silver particles, sliver halide, silver complex compound, or a silver ion. The phase states such as a solid state, a state solubilized to liquid, a gas state, and charge state types such as neutral, anionic or cationic are not particularly considered.

(Basic Structure of Cell)

FIG. 1 is a schematic sectional view showing the basic structure of the display element of the present invention.

In FIG. 1, the display apparatus of the present invention has electrolyte layer 2 sandwiched between paired counter electrodes 1, and by applying voltage or electric current to the counter electrodes via power source 3, silver contained in electrolyte layer 2 undergoes a dissolution reaction or deposition reaction. The display element varies the display state utilizing the difference in optical properties of light transmission and absorption of the compound containing silver.

(White Porous Scattering Compounds)

In the display element of the present invention, it is preferable that the electrolyte containing the room temperature molten salt according to the present invention contains white porous scattering compounds.

Examples of white porous scattering compounds usable in the present invention include titanium dioxide (being either an anatase type or a rutile type), barium sulfate, calcium carbonate, aluminum oxide, zinc oxide, magnesium oxide, zinc hydroxide, magnesium hydroxide, magnesium phosphate, magnesium hydrogenphosphate, alkaline earth metal salts, talc, kaolin, zeolite, acid clay, glass, and organic compounds such as polyethylene, polystyrene, acrylic resins, ionomers, ethylene-vinyl acetate copolymers, benzoguanamine resins, urea-formalin resins, melamine-formalin resins, or polyamide resins, which may be employed individually or in a composite mixture, or in a state having voids which alter the refractive index in particles.

In the present invention, of the above white porous scattering compounds, preferably employed are titanium dioxide, zinc oxide, and zinc hydroxide. Further usable are titanium dioxide which has been subjected to a surface treatment employing inorganic oxides (such as $Al_2O_3$, AlO(OH), or $SiO_2$) and titanium dioxide which is subjected to a treatment employing organic compounds such as trimethylolethane, triethanolamine acetic acid salt, or trimethylcyclosilane in addition to the above surface treatment.

Of these white porous scattering compounds, in view of minimizing coloration at high temperature, and reflectance of elements due to the refractive index, it is more preferable to employ titanium oxide or zinc oxide.

The above white porous scattering compounds are incorporated into an electrolyte by such a method as follows. For example, dispersion is conducted in the presence of the room temperature molten salts according to the present invention, employing a homogenizer (for example, an ultrasonic homogenizer or a high speed stirrer), whereby it is possible to supply the white porous scattering compounds as a dispersion in which they are dispersed in the room temperature molten salts.

([X]/[Ag])

In the display element of the present invention, it is preferable to satisfy the conditions specified by following Formula (1):

$$0 \leq [X]/[Ag] \leq 0.01 \qquad \text{Formula (1)}$$

wherein [X] represents mol concentration (mol/kg) of halogen ions or halogen atoms contained in the electrolyte, and [Ag] represents total mol concentration (mol/kg) of silver or compounds containing silver in the chemical structure, contained in the above electrolyte.

Halogen atoms, as described in the present invention refer to any of the iodine, chloride, bromine, and fluorine atoms. When [X]/[Ag] is at least 0.01, during oxidation-reduction reaction of silver, $X^- \rightarrow X_2$ occurs. This reaction becomes one of the factors in which $X_2$ easily undergoes cross oxidation with blackened silver to dissolve blackened silver, resulting in a decrease in memory capability. Consequently, it is preferable that the mol concentration of halogen atoms is as low as possible with respect to the mol concentration of silver. In the present invention, $0 \leq [X]/[Ag] \leq 0.001$ is more preferred. When halogen ions are added, in view of enhancement of memory capability, the sum of mol concentration of each of the halogen species is [I]<[Br]<[Cl]<[F].

(Electrolyte—Silver Salt)

In the display element of the present invention, employed may be known silver compounds such as silver iodide, silver chloride, silver bromide, silver oxide, silver sulfide, silver citrate, silver acetate, silver behenate, silver p-toluenesulfonate, silver salts of mercapto compounds, and silver complexes of iminodiacetic acids. Of these, it is preferable to employ silver salts which have no nitrogen atom exhibiting coordination capability with halogen, carboxylic acid, and silver, and for example, preferred is silver p-toluenesulfonate.

Silver ion concentration in the electrolyte according to the present invention is preferably 0.2 mol/kg≦[Ag]≦2.0 mol/kg. When the silver ion concentration is at most 0.2 mol/kg, a diluted silver solution is formed to lower the driving rate, while when it exceeds 2 mol/kg, solubility is degraded to tend to result in inconvenience of deposition during storage at low temperature.

(Electrolyte Materials)

In the display element of the present invention the electrolyte may contain the following compounds when the electrolyte is liquid. Listed as potassium compounds are KCl, KI, and KBr, as lithium compounds are $LiBF_4$, $LiClO_4$, $LiPF_6$, and $LiCF_3SO_3$, and as tetraalkylammonium compounds are tetraethylammonium perchlorate, tetrabutylammonium perchlorate, tetraethylammonium borofluoride, tetrabutylammonium borofluoride, and tetrabutylammonium halide. Further, it is possible to preferably employ a molten salt electrolytic composition described in Paragraphs of JP-A 2003-187881. Further, it is possible to employ compound, which becomes an oxidation-reduction pair such as $I^-/I_3^-$, $Br^-/Br_3^-$, or quinone/hydroquinone.

Further, the electrolyte may contain the following compounds exhibiting electronic conductivity and ionic conductivity, when a supporting electrolyte is solid.

Such compounds include a vinyl fluoride based polymer containing perfluorosulfonic acid, polythiophene, polyaniline, polypyrrole, triphenylamines, polyvinyl carbazoles, polymethylphenylsilanes, chalcogenides such as $Cu_2S$, $Ag_2S$, $Cu_2Se$, or $AgCrSe_2$, fluorine-containing compounds such as $CaF_2$, $PbF_2$, $SrF_3$, $LaF_3$, $TlSn_2F_5$, or $CeF_3$, Li salts such as $Li_2SO_4$, $Li_4SiO_4$, or $Li_3PO_4$, $ZrO_2$, CaO, $Cd_2O_3$, $HfO_2$, $Y_2O_3$, $Nb_2O_5$, $WO_3$, $Bi_2O_3$, AgBr, AgI, CuCl, CuEr, CuI, LiI, LiBr, LiCl, $LiAlCl_4$, $LiAlF_4$, AgSBr, $C_5H_5NHAg_5I_6$, $Rb_4Cu_{16}I_7Cl_{13}$, $Rb_3Cu_7Cl_{10}$, LiN, $Li_5NI_2$ and $Li_6NBr_3$.

Further, it is possible to employ a gel-like electrolyte as a supporting electrolyte. When the electrolyte is non-aqueous, it is possible to employ oil gelling agents described in Paragraphs [0057]-[0059] of JP-A H11-185836.

(Thickener Added to Electrolyte)

In the display element of the present invention, along with a polysaccharide thickener according to the present invention, it is possible to simultaneously employ a thickener known in the art ass for as the objects and effects of the present invention are not adversely affected. Examples thereof include gelatin, gum Arabic, poly(vinyl alcohol), hydroxyethyl cellulose, hydroxypropyl cellulose, cellulose acetate, cellulose acetate butyrate, poly(vinylpyrrolidone), poly(alkylene glycol), casein, starch, poly(acrylic acid), poly(methylmethacrylic acid), poly(vinyl chloride), poly(methacrylic acid), copoly(styrene-maleic anhydride), copoly(styrene-acrylonitrile), copoly(styrene-butadiene), poly(vinyl acetals), for example, poly(vinyl formal and poly(vinyl butyral), poly(esters), poly(urethanes), phenoxy resins, poly(vinylidene chloride), poly(epoxides), poly(carbonates), poly(vinyl acetate), cellulose esters, poly(amides). Hydrophobic transparent binders include polyvinyl butyral, cellulose acetate, cellulose acetate butyrate, polyester, polycarbonate, polyacrylic acid, and polyurethane.

These thickeners may be employed in combinations of at least two types. Further listed may be the compounds described on pages 71-75 of JP-A S64-13546. In view of enhancement of compatibility with various additives and dispersion stability of white particles, of these, preferably employed compounds include polyvinyl alcohols, polyvinylpyrrolidones, hydroxypropyl celluloses, and polyalkylene glycols.

(Other Additives)

Constituting layers of the display element of the present invention may include subsidiary layers such as a protective layer, a filter layer, an antihalation layer, a cross-over light cutting layer, or a backing layer. If desired, may be incorporated in these subsidiary layers are various types of chemical sensitizers, noble metal sensitizers, sensitizing dyes, supersensitizing dyes, couplers, high-boiling point solvents, antifoggants, stabilizers, development restrainers, bleach accelerators, fixing accelerators, color mixing inhibitors, formalin scavengers, toning agents, hardeners, surface active agents, thickeners, plasticizers, lubricants, UV absorbers, anti-irradiation dyes, filter light absorbing dyes, fungicides, polymer latexes, heavy metals, antistatic agents, and matting agents.

These additives, described above, are detailed in Research Disclosure (hereinafter referred to as RD), Volume 176 Item/17643 (December 1978), Volume 184 Item/18431 (August 1979), Volume 187 Item/18716 (November 1979), and Volume 308. (December 1989).

Types and listed positions of the compounds cited in these three Research Disclosures are described below.

| Additive | RD 17643 Page & Class | RD 18716 Page & Class | RD 308119 Page & Class |
|---|---|---|---|
| Chemical Sensitizer | 23 III | 648 upper right | 96 III |
| Sensitizing Dye | 23 IV | 648-649 | 996-8 IV |
| Desensitizing Dye | 23 IV | | 998 IV |
| Dye | 25-26 VIII | 649-650 | 1003 VIII |
| Development Accelerator | 29 XXI | 648 upper right | |
| Antifoggant, Stabilizer | 24 IV | 649 upper right | 1006-7 VI |
| Whitening Agent | 24 V | | 998 V |

-continued

| Additive | RD 17643 Page & Class | RD 18716 Page & Class | RD 308119 Page & Class |
|---|---|---|---|
| Hardener | 26 X | 651 upper left | 1004-5 X |
| Surface Active Agent | 26-7 XI | 650 right | 1005-6 XI |
| Antistatic Agent | 27 XII | 650 right | 1006-7 XIII |
| Plasticizer | 27 XII | 650 right | 1006 XII |
| Lubricant | 27 XII | | |
| Matting Agent | 28 XVI | 650 right | 1008-9 XVI |
| Binder | 26 XXII | | 1003-4 IX |
| Support | 28 XVII | | 1009 XVII |

(Layer Configuration)

Constitution layers between the counter electrodes of the display element of the present invention will further be described.

As the constitution layer related to the display element of the present invention, it is possible to provide a constitution layer containing a positive hole transporting material. Examples of positive hole transporting materials include aromatic amines, triphenylene derivatives, oligothiophene compounds, polypyrroles, polyacetylene derivatives, polyphenylene vinylene derivatives, polythienylene vinylene derivatives, polythiophene derivatives, polyaniline derivatives, polytoluidine derivatives, CuI, CUSCN, $CuInSe_2$, $Cu(In,Ga)Se$, $CuGaSe_2$, $Cu_2O$, CuS, $CuGaS_2$, $CuInS_2$, GaP, NiO, CoO, FeO, $Bi_2O_3$, $MoO_2$, and $Cr_2O_3$.

(Substrates)

Preferably employed as substrates usable in the present invention may be synthetic plastic films composed, for example, of polyolefins such as polyethylene or polypropylene, polycarbonates, cellulose acetate, polyethylene terephthalate, polyethylenedinaphthalene dicarboxylate, polyethylene naphthalates, polyvinyl chloride, polyimide, polyvinyl acetals, or polystyrene. Further, preferred are syndiotactic-structured polystyrenes. It is possible to prepare these employing the methods described, for example, in JP-A S62-117708, H01-46912, and H01-178505. Further listed are metal substrates of stainless steel, paper supports such as baryta paper or resin-coated paper, supports composed of the above plastic film having thereon a reflection layer, and those described, as a support, in JP-A S62-253195 (pages 29-31). It is possible to preferably employ those described on page 28 of RD No. 17643, from the light column on page 647 to the left column on page 648 of RD No. 18716, and on page 879 of RD No. 307105. As described in U.S. Pat. No. 4,151,735, these supports may be subjected to a thermal treatment at a temperature below Tg so that core-set curl is minimized. Further, the surface of these supports may be subjected to a surface treatment with the aim of enhancement of adhesion of the support to another constitution layer. In the present invention employed as a surface treatment may be a glow discharge treatment, an ultraviolet radiation treatment, a corona treatment, and a flame treatment. Further employed may be supports described on pages 44-149 of Kochi Gijutsu (Known Technology) No. 5 (published by AZTEC Japan., Mar. 22, 1991). Further listed are those described on page 1009 of RD No. 308119, as well as in the item "Supports" on page 108 of Product Licensing Index Volume 92. Other than the above, employed may be glass substrates and epoxy resins kneaded with glass powder.

(Electrode)

In the display element of the present invention, it is preferable that at least one of the counter electrodes is a metal electrode. Employed as a metal electrode may be metals such as platinum, gold, silver, copper aluminum, zinc, nickel, titanium, or bismuth, as well as alloys thereof, which are known in the art. Preferred metals employed in the metal electrodes are those which exhibit a work function near the oxidation-reduction potential of silver in the electrolyte. Of these, a silver electrode or an electrode composed of silver in an amount of at least 80% is advantageous to maintain reduced silver, and further, results in anti-staining of electrodes. Employed as a method to prepare the electrodes may be conventional ones such as a vacuum evaporation method, a printing method, an ink-jet printing method, a spin coating method, or a CVD method.

Further, it is preferable that in the display element of the present invention, at least one of the counter electrodes is transparent. Transparent electrodes are not particularly limited as long as they are transparent and electrically conductive. Examples thereof include indium tin oxide (ITO), indium zinc oxide (IZO), fluorine-doped tin oxide (FTO), indium oxide, zinc oxide, platinum, gold, silver, rhodium, copper, chromium, carbon, aluminum, silicon, amorphous silicon, and BSO (bismuth silicon oxide). In order to form electrodes, as described above, for example, an ITO layer may be subjected to mask evaporation on a substrate employing a sputtering method, or after forming an ITO layer on the entire surface, patterning may be performed employing photolithography. The surface resistance value is preferably at most 100Ω/□, but is more preferably at most 10Ω/□. The thickness of the transparent electrode is not particularly limited, but is commonly 0.1-20 μm.

(Other Constituting Components of Display Element)

If desired, employed in the display element of the present invention may be sealing agents, columnar materials, and spacer particles.

Sealing agents are those which perform sealing so that leak to the exterior is minimized, and are called sealants. Employed as sealing agents may be heat curing, light curing, moisture curing, and anaerobic during type resins such as epoxy resins, urethane based resins, acryl based resins, vinyl acetate based resins, en-thiol based resins, silicone based resins, or modified polymer resins.

Columnar materials provide a strong self-supporting capability (strength) between substrates. For example, listed may be a cylindrical form, a quadrangular form, an elliptic from, and a trapezoidal form which are arranged at definite intervals in a specified pattern such as a lattice. Further employed may be stripe-shaped ones arranged at definite intervals. It is preferable that the columnar materials are not randomly arranged but arranged at an equal distance so that the interval gradually varies, or a predetermined pattern is repeated at a definite cycle so that the distance between substrates is nearly maintained and image display is not degraded. When the columnar materials are such that the ratio of the area occupied by the display region of a display element is 1-40%, sufficient strength as a display element for commercial viability is obtained.

In order to maintain a uniform gap between paired substrates, provided between them may be spacers. As such spacers, exemplified may be spheres composed of resins or inorganic oxides. Further suitably employed are adhesion spacers, the surface of which is coated with thermoplastic resins. In order to maintain a uniform gap between substrates, provide only may be columnar materials. However, both spacers and columnar materials may be provided. Instead of the columnar materials, only spacers may be employed as space-maintaining members. The diameter of spacers, when a columnar material is formed, is at most its height, but is preferably equal to the above height. When no columnar material is formed, the diameter of spacers corresponds to the thickness of the cell gap.

(Screen Printing)

In the present invention, it is possible to form sealing agents, columnar materials, and electrode patterns, employing a screen printing method. In screen printing methods, a screen, on which predetermined patterns are formed, is applied onto the electrode surface, and printing materials (compositions to form columnar materials such as light-curing resins) are placed on the screen. Subsequently, a squeegee is moved at a predetermined pressure, angle and rate. By such action, the printing materials are transferred onto the above substrate via the pattern of the screen. Subsequently, the transferred materials are thermally cured and dried. When columnar materials are formed employing the screen printing method, resinous materials are not limited to light-curing resins, but also employed, for example, may be heat curable resins such as epoxy resins or acryl resins, as well as thermoplastic resins. Listed as thermoplastic resins are: polyvinyl chloride resins, polyvinylidene chloride resins, polyvinyl acetate resins, polymethacrylic acid ester resins, polyacrylic acid ester resins, polystyrene resins, polyamide resins, polyethylene resins, polypropylene resins, fluororesins, polyurethane resins, polyacrylonitrile resins, polyvinyl ether resins, polyvinyl ketone resins, polyether resins, polyvinylpyrrolidone resins, saturated polyester resins, polycarbonate resins, and chlorinated polyether resins. It is preferable that resinous materials are employed in the form of a paste, while dissolved in suitable solvents.

As noted above, after forming the columnar materials on the substrate, if desired, a spacer is provided on at least one side of the substrate, and paired substrates are placed so that the electrode forming surfaces face each other, whereby a vacant cell is formed. By heating the paired facing substrates, under application of pressure from both sides, they are adhered to each other, whereby a display cell is obtained. Preparation of a display element may be achieved by injecting an electrolyte composition between the substrates, employing a vacuum injection method. Alternatively, during adhesion of the substrates, an electrolyte composition may be dripped onto the surface of one of the substrates and then a liquid crystal composition is injected simultaneously sealed when the substrates are adhered to each other.

(Method to Drive Display Element)

In the display element of the present invention, it is preferable to drive a display element so that blackened silver is deposited via voltage application of at least deposition overvoltage and deposition of blackened silver is allowed to continue via application of voltage lower than the deposition overvoltage. By performing the above driving operation, it is possible to lower energy for writing, decrease the driving circuit load, as well as to enhance writing rate. It is common knowledge that during the electrode reaction in the electrochemical field, overvoltage exists. Overvoltage is detailed, for example, on page 121 of "Denshi Ido no Kagaku—Denkikagaku Nyumon (Chemistry of Electron Transfer—Introduction to Electrochemistry)" (1996, published by Asakura Shoten). It is possible to consider that the display element of the present invention undergoes an electrode reaction of an electrode with silver in the electrolyte. Consequently, it easy to understand the presence of overvoltage during silver dissolution and deposition. Since the magnitude of overvoltage is controlled by exchange current density, it is assumed that the fact that as shown in the present invention, after formation of blackened silver, deposition of blackened silver continues via application of voltage lower than the deposition overvoltage, is that the surface of the blackened silver results in less excessive electric energy, whereby it is possible to easily perform electron injection.

Driving operation of the display element of the present invention may be simple matrix driving or active matrix driving. Simple matrix driving, as described in the present invention, refers to the driving method in which electric current is sequentially applied to a circuit in which a positive electrode line containing a plurality of positive electrodes faces a negative electrode line containing a plurality of negative electrodes so that each line intersects in the perpendicular direction. By employing simple matrix driving, it is possible to simplify the circuit structure and the driving IC, resulting in advantages such as lower production cost. Active matrix driving refers to a system in which scanning lines, data lines, and current feeding lines are formed in a checkered pattern and driving is performed by TFT circuits arranged in each of the squares of the checkered pattern. Since it is possible to switch for each pixel, advantages result in gradation as well as memory function. For example, it is possible to employ the circuit described in FIG. 5 of JP-A No. 2004-29327.

(Applied Products) It is possible to apply the display element of the present invention to electronic book related fields, ID card related fields, public information related fields, transportation related fields, broadcasting related fields, account settling fields, and distribution and logistics related fields. Specific examples include door keys, student identification cards, employee ID cards, various club membership cards, convenience store cards, department store cards, vending machine cards, gas station cards, subway and railroad cards, bus cards, cash cards, credit cards, highway cards, driver licenses, hospital medical examination cards, health insurance cards, Basic Resident Registers, passports, and electronic books.

EXAMPLES

The present invention will now be specifically described with reference to examples, however the present invention is not limited thereto. In the examples, "parts" or "%" is used and represents "parts by weight" or "% by weight", respectively, unless otherwise specified.

Example 1

Preparation of Room Temperature Molten Salts (Preparation of Room Temperature Molten Salt 1)

Silver bromide and Exemplified Compound (I-12) were mixed at a mol ratio of 1:3. The resulting mixture was heated at 150° C. for one hour. After confirming a molten state in which no powders remained, the temperature was gradually lowered to 25° C., whereby Room Temperature Molten Salt 1 was prepared, which remained in a molten state even at room temperature.

(Preparation of Room Temperature Molten Salt 2)

Silver iodide and Exemplified Compound (I-19) were mixed at a mol ratio of 1:3. After dissolving the resulting mixture in dimethylsulfoxide in an amount by a factor of 100, the resulting solution was heated at 150° C. for one hour under reduced pressure to remove dimethylsulfoxide via evaporation. Thereafter, the temperature was gradually lowered to 25° C., whereby Room Temperature Molten State 2 was prepared which remained in a molten state even at room temperature.

(Preparation of Room Temperature Molten Salt 3)

Silver p-toluenesulfonate and Exemplified Compound (II-3) were mixed at a weight ratio of 2:3, and the resulting mixture was heated at 150° C. for one hour. After confirming the molten state in which no powders remained, the temperature was gradually lowered to 25° C., whereby Room Temperature Molten Salt 3 was prepared which remained in a molten state even at room temperature.
(Preparation of Room Temperature Molten Salt 4)

Silver p-toluenesulfonate and Exemplified Compound (I-12) were mixed at a mol ratio of 2:3, and the resulting mixture was heated at 120° C. for one hour. After confirming the molten state in which no powders remained, the temperature was gradually lowered to 25° C., whereby Room Temperature Molten Salt 4 was prepared which remained in a molten state even at room temperature.
(Preparation of Room Temperature Molten Salt 5)

Silver p-toluenesulfonate and Exemplified Compound (II-6) were mixed at a weight ratio of 2:3, and the resulting mixture was heated at 180° C. for one hour. After confirming the molten state in which no powders remained, the temperature was gradually lowered to 25° C., whereby Room Temperature Molten Salt 5 was prepared which remained in a molten state even at room temperature.
(Preparation of Room Temperature Molten Salt 6)

Silver p-toluenesulfonate and Exemplified Compounds (II-12) and (I-12) were mixed at a weight ratio of 2:3:0.05, and the resulting mixture was heated at 150° C. for one hour. After confirming the molten state in which no powders remained, the temperature was gradually lowered to 25° C., whereby Room Temperature Molten Salt 6 was prepared which remained in a molten state even at room temperature.
<<Preparation of Display Elements>>

Preparation of Display Element 1

Comparative Example

Preparation of Electrolyte 1

Added into 2.5 g of dimethylsulfoxide were 210 mg of potassium iodide and 300 mg of silver iodide. After complete dissolution, 0.5 g of titanium oxide (at an average primary particle diameter of 0.34 μm) was added and the resulting mixture was dispersed via an ultrasonic homogenizer. Thereafter added was 150 mg of polyvinylpyrrolidone (at an average molecular weight of 15,000), and the resulting mixture was heated while stirring at 120° C. for one hour, whereby Electrolyte 1 was prepared.
(Preparation of Transparent Electrode)

An indium oxide (ITO) film of a pitch of 145 μm and an electrode width of 130 μm was formed on a 1.5 mm thick 2 cm×4 cm glass substrate, employing the method known in the art, whereby a transparent electrode (Electrode 1) was prepared.
(Preparation of Metal Electrode)

A silver electrode (Electrode 2) of an electrode thickness of 0.8 μm, a pitch of 145 μm, and an electrode distance of 130 μm was prepared on a 1.5 mm thick 2 cm×4 cm glass substrate, employing a method known in the art.
(Preparation of Display Elements)

Electrodes 1 and 2 were arranged via a 30 μm spacer so that the electrode surfaces faced each other, and the periphery of a pattern electrode was sealed via an epoxy based sealing agent, except for the sealing inlet, whereby an empty cell was prepared. Above Electrolyte 1 was injected into the above empty cell employing a vacuum injection method. Thereafter, the sealing inlet was sealed, whereby Display Element 1 was prepared.

(Preparation of Display Elements 2-7: Present Invention)
(Preparation of Electrolyte 2)

After adding 30% by weight of titanium oxide (at an average particle diameter of 0.34 μm) to Room Temperature Electrolyte 1, titanium oxide was dispersed employing an ultrasonic homogenizer, whereby Electrolyte 2 was prepared.
(Preparation of Electrolytes 3-6)

Electrolytes 3-6 were prepared in the same manner as above Electrolyte 2, except that Room Temperature Molten Salt 1 was replaced with each of Room Temperature Molten Salts 2-5.
(Preparation of Electrolyte 7)

Electrolyte 7 was prepared in the same manner as Electrolyte 6, except that 10% by weight of propylene carbonate was added.
(Preparation of Electrolyte 8)

Electrolyte 8 was prepared in the same manner as above Electrolyte 2, except that Room Temperature Molten Salt 1 was replaced with Room Temperature Molten Salt 6.
(Preparation of Display Elements)

Display Elements 2-8 were prepared in the same manner as above Display Element 1, except that Electrolyte 1 was replaced with each of Electrolytes 2-8.
<<Evaluation of Display Elements>>
(Evaluation of Durability)

By applying ±1.5 V to each display element prepared as above, an application period (Half Reduction Period 1) during which reflectance at 550 nm was reduced by half, was determined, employing spectral calorimeter CM-3700d produced by Konica Minolta Sensing, Inc. Subsequently, after forced aging for two weeks in a hydrothermostat at 80° C. and 45? relative humidity, the application period (Half Reduction Period 2) during which reflectance at 550 nm was reduced by half, was determined, employing the same method as above.

The half reduction period ratio (Half Reduction Period 2/Half Reduction Period 1) was obtained and the resulting value was employed as an index for durability. As the numeric value approaches 1.00, durability increases. Table 1 shows the results.

TABLE 1

| Display Element No. | Evaluation of Durability (Ratio of Half Reduction Period) | Remarks |
|---|---|---|
| 1 | 1.53 | Comparative Example |
| 2 | 1.23 | Present Invention |
| 3 | 1.21 | Present Invention |
| 4 | 1.05 | Present Invention |
| 5 | 1.11 | Present Invention |
| 6 | 1.14 | Present Invention |
| 7 | 1.30 | Present Invention |

As can clearly be seen from the results listed in Table 1, display elements employing the room temperature molten salt of the present invention resulted in minimal variation range of the half reduction value even after forced aging, compared to Comparative Example, and exhibited excellent durability. Further, after forced aging in a hydrothermostat at 80° C. and 45% relative humidity for one month, the sealed portion of each display element was visually observed. In Display Elements 1 and 7, particularly Display Element 1, a trace leakage of the electrolyte around the sealed portion, and mingle of air bubbles were confirmed. On the other hand, no leakage of the electrolyte was noticed in Display Element 2-6 and 8 of the present invention.

The invention claimed is:

1. A salt composed of a silver salt and a compound represented by the Formulas (I) or (II),

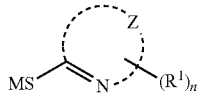

Formula (I)

wherein M represents a hydrogen atom, a metal atom, or a quaternary ammonium; Z represents a nitrogen containing heterocyclic ring excluding imidazole rings; n represents 0-5; $R^1$ represents a hydrogen atom, a halogen atom, an alkyl group, an aryl group, an alkylcarbonamido group, an arylcarbonamido group, an alkylsulfonamido group, an arylsulfonamido group, an alkoxy group, an aryloxy group, an alkylthio group, an arylthio group, an alkylcarbamoyl group, an arylcarbamoyl group, a carbamoyl group, an alkylsulfamoyl group, an arylsulfamoyl group, a sulfamoyl group, a cyano group, an alkylsulfonyl group, an arylsulfonyl group, an alkoxycarbonyl group, an aryloxycarbonyl group, an alkylcarbonyl group, an arylcarbonyl group, an acyloxy group, a carboxyl group, a carbonyl group, a sulfonyl group, an amino group, a hydroxyl group, or a heterocyclyl group; and when n is at least 2, any two or more of $R^1$ may be same or different and may be joined together to form a condensed ring,

  Formula (II)

wherein $R^2$ and $R^3$ each represent a substituted or unsubstituted hydrocarbon group, provided that when a ring containing an S atom is formed, an aromatic group is not included, and the atom adjacent to the S atom of $R^2$ and $R^3$ is not S, wherein the salt is a molten liquid at room temperature.

2. The salt of claim 1, wherein a condition specified by the Formula (3) is satisfied,

  Formula (3)

wherein M (in mol) represents a number of total mole of silver incorporated in the room temperature molten salt and S (in mol) represents a number of total enols of the compound represented by Formulas (I) or (II).

3. The salt of claim 1, wherein a condition specified by following Formula (4) is satisfied, $0 \leq (X)/(Ag) \leq 0.01$   Formula (4)

wherein (X) (in mol/kg) represents mol concentration of a halogen ion or a halogen atom incorporated in the room temperature molten salt, and (Ag) (in mol/kg) represents the total mol concentration of silver or silver in a compound containing silver in the chemical structure in the room temperature molten salt.

4. The salt as described in claim 1, which is characterized in that the compound described by aforesaid Formula (I) is a mercaptotriazole derivative.

5. The salt of claim 1, wherein a molecular weight of the compound represented by the Formula (II) is 100-250.

6. A display element comprising a pair of electrodes, an electrolyte containing silver or a compound containing silver in a chemical structure between the pair of electrodes, wherein the electrolyte contains the salts of claim 1.

7. The display element of claim 6, wherein the electrolyte contains substantially no organic solvent.

8. The display element of claim 6, wherein the electrolyte contains an organic solvent in the electrolyte is at most 5.0% by weight.

9. The display element of claim 8, wherein the electrolyte contains the organic solvent is at most 1.0% by weight.

10. The display element of claim 6, wherein the electrodes are operated to result in dissolution and deposition of silver, and the driving operation initiates blackened silver deposition via application of voltage equal to or higher than the deposition overvoltage and continues deposition of blackened silver via application of voltage equal to or lower than the deposition overvoltage.

11. The display element of claim 10 wherein the driving operation is active matrix driving.

12. The salt as described in claim 2, which is characterized in that the compound described by aforesaid Formula (I) is a mercaptotriazole derivative.

13. The salt as described in claim 3, which is characterized in that the compound described by aforesaid Formula (I) is a mercaptotriazole derivative.

14. The salt as described in claim 1, wherein the salt has a melting point of at most 25° C.

15. The salt as described in claim 14, wherein the salt has a melting point of at most 0° C.

16. The salt as described in claim 15, wherein the salt has a melting point of at most −10° C.

* * * * *